United States Patent [19]
Thornfeldt et al.

[11] Patent Number: 5,760,096
[45] Date of Patent: Jun. 2, 1998

[54] POTENT PENETRATION ENHANCERS

[76] Inventors: Carl R. Thornfeldt, 221 Crestview Dr., Nampa, Id. 83686; Peter M. Elias, Box 601, Star Rte., Muir Beach, Calif. 94965

[21] Appl. No.: 734,053

[22] Filed: Oct. 18, 1996

[51] Int. Cl.[6] ........................................ A61K 37/02
[52] U.S. Cl. ............................... 514/946; 514/947
[58] Field of Search ............................ 514/946, 947

[56] References Cited

U.S. PATENT DOCUMENTS

| | | | |
|---|---|---|---|
| 5,238,993 | 8/1993 | Catz et al. | 514/236.2 |
| 5,614,178 | 3/1997 | Bloom et al. | 424/60 |

*Primary Examiner*—Keith MacMillan
*Attorney, Agent, or Firm*—Townsend and Townsend and Crew LLP

[57] ABSTRACT

The epidermal permeability barrier to systemically and/or topically active agents or compositions designed for topical administration is enhanced to an unexpected degree by certain combinations of known penetration enhancing excipients. One group of combinations comprise a glycol and an alcohol at a weight ratio within the range of 1:0.1 to 1:10 with one or more further additives, selected from the excipient groups of branched-chain esters of fatty acids, surfactants, and membrane fluidizers. Another group of combinations comprise an alcohol of four or more carbon atoms and one or more further additives selected from the excipient groups of glycols and surfactants.

76 Claims, No Drawings

POTENT PENETRATION ENHANCERS

This invention resides in the technical field of topical formulations for delivering drugs, nutrients, antioxidants, herbal preparations, or other beneficial agents to the body of a terrestrial mammal into and through the skin or mucous membranes. In particular, this invention relates to methods of and compositions for enhancing the penetration of these agents past the epidermal barrier for systemic and/or topical administration.

BACKGROUND OF THE INVENTION

In formulations designed for the topical and/or transdermal delivery of therapeutic and other biologically active compounds, two of the most frequently used agents (excipients) for enhancing penetration of the stratum corneum barrier are propylene glycol and ethanol. Other agents used for delivery purposes include surfactants such as laurylamide and sodium dodecyl (lauryl) sulfate, branched-chain esters of fatty acids such as isopropyl myristate, membrane fluidizers such as oleyl alcohol, keratolytics such as lactic and other α-hydroxy acids and salicylic acid, and solvents such as acetone.

A potent penetration enhancer particularly designed for transepidermal activity is laurocapram (1-dodecylazacycloheptan-2-one, AZONE™, U.S. Pat. No. 4,405,616). No product with this compound as a delivery agent has been introduced to the market, however. Dimethyl sulfoxide (DMSO) is another potent penetration enhancer that is not in any approved nor legally marketed products.

A major reason for insufficient transport across the epidermal barrier is the action of various epidermal cytokines, growth factors, neuropeptides, and ions released by a disrupted stratum corneum. These signaling molecules stimulate an epidermal reparative response that is directly proportional to the degree of barrier disruption. Severe and/or prolonged disruption induces an exaggerated reparative response, clinically manifested as a contact irritant dermatitis, a condition that afflicts up to 70% of the patients using one approved transdermal patch. This contact irritant reaction limits the type, potency, and amount of barrier disrupting penetration enhancers that can be included in a drug formulation. Isopropyl myristate and propylene glycol, for example, do not induce irritant reactions at concentrations below 30%.

SUMMARY OF THE INVENTION

It has now been discovered that certain combinations of known penetration enhancing excipients, and in some cases, at certain ratios of multiple excipients in one formulation, significantly increase the permeability of the drug, nutrient, antioxidant, or other beneficial agent, while minimizing or eliminating irritation of the skin or mucus membrane. The various excipients increase the stratum corneum barrier permeability by different mechanisms of action, as demonstrated by (1) differences in how much the permeability is increased, (2) the time of onset of the increased permeability, and (3) the duration of the increased permeability. The formulations of this invention cause little or no cutaneous irritation as demonstrated by lack of observed erythema even with high amounts of barrier disruptions measured by transepidermal water loss (TEWL) of 300–900. With virtually complete disruption (TEWL≧900), mild erythema occurred as expected.

In one group of formulations within the scope of this invention, the formulations contain combinations of a glycol and an alcohol at a weight ratio within the range of about 1:0.1 to about 1:10 (glycol: alcohol), and preferably with one or more additional components selected from three other different excipient groups: surfactants, branched chain esters of fatty acids, and membrane fluidizers. Another group of formulations within the scope of this invention are those containing alcohols of four or more carbon atoms (i.e., butyl alcohol and longer chain alcohols), combined with one or more additional components selected from the glycol and surfactant groups. Further combinations and compositions will be apparent from the description that follows. This invention resides both in these penetration enhancing compositions, and in methods of using these compositions for enhancing the topical administration of systemically and/or topically active drugs and other biologically active agents including nutrients, antioxidants, herbal preparations and cosmetic ingredients.

DETAILED DESCRIPTION OF THE INVENTION AND PREFERRED EMBODIMENTS

The term "glycol" as used in this specification refers to polyhydric alcohols, preferably dihydric alcohols. Examples are ethylene glycol, propylene glycol, butylene glycol, glycerol, diethylene glycol, triethylene glycol, and polyethylene glycol. Preferred glycols are propylene glycol, diethylene glycol, and polyethylene glycol. The most preferred is propylene glycol.

The term "alcohol" refers to a monohydric alcohol, preferably an aliphatic alcohol and more preferably a $C_1$–$C_{18}$ saturated monohydric aliphatic alcohol. Examples are methanol, ethanol, propanol, isopropanol, and octanol. Among these, methanol, ethanol, and octanol are preferred, with ethanol and octanol the most preferred. An additional group of preferred alcohols are $C_4$–$C_{18}$ saturated aliphatic alcohols.

The weight ratio of glycol to alcohol in accordance with this invention is within the range of about 1:0.1 to about 1:10. In preferred embodiments, the ratio range is from about 1:1 to about 1:7.

The additional one or more components for the glycol/alcohol formulations are selected from the excipient groups of surfactants, branched-chain esters of fatty acids and membrane fluidizers. Examples of surfactants are laurylamide, lauryl sarkosine, sodium dodecyl sulfate (SDS), dodecyl benzene sulfonate, and cocamidopropyl betaine. Among these, laurylamide, lauryl sarkosine, and SDS are most preferred. Preferred branched-chain esters of fatty acids are isopropyl esters of $C_7$–$C_{24}$ fatty acids. The most preferred branched-chain esters of fatty acids are isopropyl myristate and isopropyl palmitate. The preferred membrane fluidizer is oleyl alcohol.

When one or more surfactants are present, they preferably amount to about 0.01% to about 25% by weight of the formulation, and most preferably from about 0.2% to about 10% by weight. A particularly preferred surfactant level is 3% by weight. When one or more branched-chain esters of fatty acids are present, they preferably amount to about 0.1% to about 50% by weight of the formulation, and most preferably from about 1.0% to about 20%. When one or more membrane fluidizers are present, they preferably constitute from about 0.1% to about 25% by weight of the formulation, and most preferably from about 1.0% to about 7.0%.

The preferred formulations of the first group of penetration enhancing compositions are:

| Major Components (abbreviation followed by parts by weight) | | Additional Components (abbreviation followed by weight percent relative to total composition) | | |
|---|---|---|---|---|
| Glycol | Alcohol | Branched-chain Ester | Surfactant | Membrane Fluidizer |
| a. PG1 | ET7 | M2 | — | OA5 |
| b. PG1 | ET7 | M2 | LS1.5 | — |
| c. PG1 | ET7 | M2 | LS3 | — |
| d. PG1 | ET7 | M2 | LS5 | — |
| e. PG1 | ET7 | M2 | LS5 | OA5 |
| f. PG1 | ET7 | M2 | LS10 | OA5 |
| g. PG1 | OC1 | — | SD3 | — |
| h. PG1 | ET2 | — | SD3 | — |
| i. PG1 | ET7 | — | SD3 | — |
| j. PG2 | ET7 | — | LR1 | — |
| k. PG2 | ET7 | — | LR3 | — |
| l. PG2 | ET7 | — | LR5 | — |
| m. PG2 | ET7 | — | LR10 | — |
| n. PG2 | ET7 | — | CB3 | — |
| o. PG2 | ET7 | P10 | — | — |
| p. PG2 | ET7 | M5 | — | — |
| q. PG2 | ET7 | M10 | — | — |
| r. PG2 | ET7 | M20 | — | — |

The most preferred formulations of this first group are:

| Major Components (abbreviation followed by parts by weight) | | Additional Components (abbreviation followed by weight percent relative to total composition) | | |
|---|---|---|---|---|
| Glycol | Alcohol | Branched-chain Ester | Surfactant | Membrane Fluidizer |
| PG1 | ET7 | M2 | LS5 | — |
| PG1 | ET7 | M2 | LS10 | OA5 |
| PG1 | ET2 | — | SD3 | — |
| PG2 | ET7 | — | LR1 | — |
| PG2 | ET7 | — | LR3 | — |
| PG2 | ET7 | P10 | — | — |
| PG2 | ET7 | M10 | — | — |

Abbreviations:

CB cocamidopropyl betaine
ET ethanol
LR laurylamide
LS lauryl sarkosine
M isopropyl myristate
OA oleyl alcohol
OC octanol
P isopropyl palmitate
PG propylene glycol
SD sodium dodecyl sulfate The preferred formulations of the second group of penetration enhancing compositions of this invention are:

(a) propylene glycol and octanol; and
(b) octanol combined with either laurylamide, SDS or lauryl sarkosine.

The most preferred of these formulations are:

(a) propylene glycol and octanol in weight ratios of 1:1, 1:3, or 1:7; and
(b) octanol combined with either 3% laurylamide or 3% SDS.

The term "systemically active agent" is used herein to refer to therapeutic drugs or other compounds or compositions that induce a biological response either upon entering the bloodstream or after having been transported by the bloodstream to a site of interest within the patient's body. Examples are anti-infectives such as antibiotics and antiviral agents, analgesics and analgesic combinations, anorexics and appetite suppressants, anthelmintics, anesthetics, antiarthritics, antiasthma agents, anticonvulsants, antidepressants, antidiabetic agents, antidiarrheals, antihistamines, anti-inflammatory agents, antimigraine preparations, antimotion sickness agents, antinauseants, antineoplastics, antiparkinsonism agents, antipruritics, antipsychotics, antipyretics, antispasmodics, anticholinergics, sympathomimetics, xanthine derivatives, cardiovascular preparations including calcium channel blockers, beta blockers, antiarrhythmics, antihypertensives, diuretics, vasodilators (general, coronary, peripheral and cerebral), central nervous system stimulants, cough and cold preparations, decongestants, diagnostics, hormones, hypnotics, immunosuppressives, muscle relaxants, parasympatholytics, parasympathomimetics, psychostimulants, sedatives, tranquilizers, antiooxidants, vitamins, minmerals, other nutrients, and herbal extracts or preparations.

The term "topically active agent" is used herein to refer to compounds that induce a biologic response in the skin or mucous membrane. Examples include anti-inflammatory agents, anti-infectives, analgesics, anesthetics, antihistamines, photoprotective agents, antineoplastics, antipruritics, neuropeptides, channel blockers, hydrocarbon compositions, hormones, vitamins, minerals, antioxidants, other nutrients, herbal extracts or preparations, and cosmetic ingredients. Certain agents listed above are active both systemically and in the skin and mucous membrane.

The formulations in which the penetration enhancers are incorporated in accordance with this invention may assume any of a variety of dosage forms. Examples are creams, lotions, gels, ointments, suppositories, sprays, aerosols, buccal and sublingual tablets and various passive and active transdermal devices for absorption through the skin and mucous membranes.

The penetration enhancing compositions of this invention may constitute a small amount of the formulation or a large amount depending on which excipient composition is used, which systemically and/or topically active agent is used and the type of biological effect sought. The amount will be readily apparent to those skilled in the art, since the total amount of penetration enhancers will be approximately the same as those of the prior art. For example, when the potency of the penetration enhancement composition is greatly increased, lower quantities can be used. In general, however, best results will be obtained with formulation in which the penetration enhancing excipients comprise from about 0.05% to about 50% by weight of the formulation, and preferably from about 0.5% to about 20% by weight.

The amount of systemically and/or topically active agent included in the formulation is subject to generally the same considerations. The appropriate amount in most cases will also be determined by the degree to which penetration enhancement is achieved. When the increase in penetration is relatively large, lesser amounts of the active agent can be used. With these considerations, the appropriate amounts or concentrations in any given instance will be readily apparent to the skilled physician prescribing the formulation or to the formulator preparing the formulation for use by the lay person.

Subjects to whom the formulations can be administered are primarily terrestrial mammals, including humans, pets, and livestock and other farm animals. The invention is of greatest interest in its application to humans.

The following examples are offered for purposes of illustration. They are intended neither to define nor to limit this invention in any manner.

EXAMPLES

Transepidermal water loss (TEWL) is recognized in the topical formulations industry as a reproducible and reliable indicator of the integrity of the stratum corneum barrier, and has been correlated with the efficacy of formulations for delivering drugs and other biologically active agents. A normal stratum corneum allows some transepidermal water loss and the amount of loss varies with the individual. This variation is compensated for by determining a baseline TEWL value and incorporating this value into TEWL measurements at selected intervals after administration of a test formulation. It is also well known that occlusion increases hydration of the stratum corneum and that this will dramatically increase penetration of topically applied compounds including certain lipophilic corticosteroids. Occlusion may potentiate any penetration enhancing system, and was therefore tested at a site that had been used in previous tests.

Tests were performed on hairless mice, aged 8 to 12 weeks, by repeated applications of various test formulations, both within and outside the scope of the invention. Multiple test sites on multiple animals were used for each formulation. The TEWL rates were measured periodically after a baseline measurement taken immediately after application, by use of an electrolytic water analyzer (Meeco, Inc., Warrington, Pa., USA). Readings taken on this instrument indicate the integrity of the stratum corneum permeability barrier. The results are shown in the table below, where the average of the multiple readings and range of variation are shown for each test at each measurement time.

The importance of the specific ratio of the alcohol and glycol is demonstrated by the difference in TEWL between a formulation containing propylene glycol (PG) and ethanol (ET) at a 7:3 ratio (Test No. 1) and one with the same components at a 3:7 ratio (Test No. 2). One hour after application, the increase in stratum corneum permeability achieved with the 3:7 ratio formulation (2.3+0.4=6.4) was nearly four times that achieved with the 7:3 formulation (3.2+2.1=1.8). Further confirmation was shown with a different alcohol. In Test No. 23, PG1:octanol (OC)1, the TEWL at 2 hours was 221, while the PG1:OC3 in Test No. 24 the TEWL exceeded 1,000. The importance of producing a synergistic penetration enhancing effect by adding the one additional excipient component is shown when 2% oleyl alcohol (OA) is added to PG7:ET3 as in Test No. 6 vs. No. 1. TEWL is increased by about 9 fold. This third component concept is confirmed with TEWL nearly doubling when 2% OA is added to ET5:M5 (where M is isopropryl myristate) 5 as in Test No. 10 vs. No. 9.

The further increased synergism of increasing barrier permeability by adding a fourth component from a different excipient group to glycol:alcohol is shown in comparing TEWL of Test No. 11 and No. 12. The TEWL at 1 hour is more than doubled (15.1+2.2=6.9 vs. 25+1.9=3.2) by adding 2% OA to PG3:ET5:M2.

Even further synergism occurred when one component selected from each of the surfactant, branched-chain ester of a fatty acid, and membrane fluidizer groups was added by comparing TEWL at 1 hour of Test No. 15 (244+23=10.6) vs. Test No. 21 (418+15=27.9). The addition of lauryl sarkosine (LS) to PG1:ET7:M2 plus 5% OA nearly doubled TEWL.

When a surfactant was present, the choice of surfactant in some cases had a significant effect on the potency of the penetration enhancing composition. Test Nos. 33, 34, 38, and 39, demonstrate that sodium dodecyl sulfate (SDS) and laurylamide (LR) were more effective than dodecyl benzene sulfonate (DB) and cocamidopropyl betaine (CB) in increasing barrier permeability. LS is a very active penetration enhancing compound which appears, superior to the membrane fluidizer OA in this system as shown in Test No. 19 vs. Test No. 15.

Not only does this invention show there is a critical weight ratio between the glycol and alcohol for optimum activity but the activity can further be enhanced by adding excipients to the composition. The excipients' optimal activity however is not predictable. For example, isopropyl myristate increases TEWL progressively as the concentration is increased (Test Nos. 46–49) as does lauryl sarkosine (Test Nos. 16–19) and oleyl alcohol (Test Nos. 6, 12, 14, vs. 7, 13, 15). On the contrary, LR activity reaches its maximum TEWL at 1–3% despite further increasing the concentration (Test Nos. 36–40) and also CB reaches its maximum at 3% despite further increasing the concentration (Test Nos. 41–44). A similar maximum peak is seen with ET in a composition of PG and SD (Test Nos. 29–31). Test No. 22 vs. 11 demonstrated the additional effect of occlusion on PG3:ET5:M2.

Erythema was recorded when observed by the investigator. It was graded on 0–4+ scale. Formulations 24, 25 and 28 produced 2+ erythema while 49 produced only 1+ erythema.

TABLE

Trans-Epidermal Water Loss Test Results

| | Components and Parts by Weight (except where marked "%" indicating weight percent) | | | Trans-Epidermal Water Loss (g/m²/h) | | | |
|---|---|---|---|---|---|---|---|
| Test No. | Glycol | Alcohol | Others | 0 Hour (Baseline) | 1 Hour | 2 Hours | 4 Hours |
| 1 | PG7 | ET3 | — | 2.1 ± 0.3 | 3.2 ± 0.3 | 2.1 ± 0.3 | — |
| 2 | PG3 | ET7 | — | 0.4 ± 0.1 | 2.3 ± 0.5 | 0.7 ± 0.1 | — |
| 3 | PG98% | — | OA2% | 0.9 ± 0.1 | 9.8 ± 1.2 | 3.0 ± 0.4 | — |
| 4 | — | ET98% | OA2% | 1.4 ± 0.1 | 1.3 ± 0.1 | 1.0 ± 0.2 | — |
| 5 | — | — | M98%, OA2% | 0.4 ± 0.0 | 2.8 ± 0.3 | 4.0 ± 0.6 | — |
| 6 | PG7 | ET3 | OA2% | 1.9 ± 0.2 | 27.5 ± 4.1 | 13.3 ± 2.0 | — |
| 7 | PG7 | ET3 | OA5% | 3.0 ± 0.2 | 41.2 ± 4.2 | 52.1 ± 10.1 | 62.3 ± 12.0 |
| 8 | PG3 | ET7 | OA2% | 1.0 ± 0.1 | 8.2 ± 2.0 | 2.4 ± 0.3 | — |
| 9 | — | ET5 | M5 | 0.9 ± 0.2 | 7.6 ± 2.0 | 9.7 ± 2.5 | — |

TABLE-continued

Trans-Epidermal Water Loss Test Results

| Test No. | Components and Parts by Weight (except where marked "%" indicating weight percent) | | | Trans-Epidermal Water Loss ($g/m^2/h$) | | | |
|---|---|---|---|---|---|---|---|
| | Glycol | Alcohol | Others | 0 Hour (Baseline) | 1 Hour | 2 Hours | 4 Hours |
| 10 | — | ET5 | M5, OA2% | 1.2 ± 0.1 | 13.0 ± 2.7 | 19.4 ± 4.5 | — |
| 11 | PG3 | ET5 | M2 | 2.2 ± 0.3 | 15.1 ± 1.6 | 5.7 ± 0.9 | — |
| 12 | PG3 | ET5 | M2, OA2% | 1.9 ± 0.3 | 25.0 ± 5.5 | 21.6 ± 7.4 | — |
| 13 | PG3 | ET5 | M2, OA5% | 2.1 ± 0.2 | 38.4 ± 8.0 | 57.4 ± 13.7 | — |
| 15 | PG1 | ET7 | M2, OA2% | 21 ± 4 | 188 ± 22 | 191 ± 26 | 133 ± 16 |
| 16 | PG1 | ET7 | M2, OA5% | 23 ± 2 | 244 ± 27 | 251 ± 37 | 246 ± 39 |
| 17 | PG1 | ET7 | M2, LS0.5% | 10 ± 1 | 100 ± 11 | 82 ± 9 | 73 ± 9 |
| 18 | PG1 | ET7 | M2, LS1.5% | 11 ± 1 | 165 ± 56 | 248 ± 47 | 234 ± 42 |
| 19 | PG1 | ET7 | M2, LS3% | 16 ± 2 | 393 ± 31 | 336 ± 30 | 279 ± 22 |
| 20 | PG1 | ET7 | M2, LS5% | 20 ± 2 | 552 ± 61 | 391 ± 22 | 437 ± 58 |
| 21 | PG1 | ET7 | M2, OA5%, LS5% | 16 ± 2 | 376 ± 34 | 330 ± 28 | 257 ± 15 |
| 22 | PG1 | ET7 | M2, OA5%, LS10% | 15 ± 2 | 418 ± 49 | 402 ± 52 | 410 ± 75 |
| 23 | PG3 | ET5 | M2 occluded | 2.2 ± 0.3 | 120 ± 14 | 78 ± 10 | 51 ± 7 |
| 24 | PG1 | OC1 | — | 14 ± 1 | — | 221 ± 40 | 213 ± 38 |
| 25 | PG1 | OC3 | — | 30 ± 3 | — | >1000 | >1000 |
| 25 | PG1 | OC7 | — | 31 ± 2 | — | >1000 | >1000 |
| 26 | — | OC97% | LR3% | 10 ± 1 | — | 390 ± 55 | 498 ± 65 |
| 27 | — | OC97% | SD3% | 16 ± 1 | — | 343 ± 63 | 345 ± 55 |
| 28 | PG1 | OC1 | SD3% | 24 ± 1 | — | >1000 | >1000 |
| 29 | PG1 | ET1 | SD3% | 24 ± 1 | — | 165 ± 25 | 114 ± 13 |
| 30 | PG1 | ET2 | SD3% | 26 ± 4 | — | 365 ± 52 | 203 ± 26 |
| 31 | PG1 | ET7 | SD3% | 19 ± 1 | — | 254 ± 32 | 209 ± 21 |
| 32 | PG1 | MT7 | — | — | — | 185 ± 23 | 187 ± 23 |
| 33 | PG2 | ET7 | SD3% | 21 ± 1 | — | 307 ± 46 | 243 ± 38 |
| 34 | PG2 | ET7 | DB3% | 16 ± 1 | — | 131 ± 24 | 109 ± 22 |
| 35 | PG2 | ET7 | LS5% | 15 ± 1 | — | 140 ± 13 | 81 ± 6 |
| 36 | PG2 | ET7 | LR0.2% | 21 ± 2 | — | 181 ± 15 | 104 ± 13 |
| 37 | PG2 | ET7 | LR1% | 26 ± 4 | — | 383 ± 85 | 242 ± 49 |
| 38 | PG2 | ET7 | LR3% | 27 ± 2 | — | 378 ± 74 | 279 ± 47 |
| 39 | PG2 | ET7 | LR5% | 32 ± 3 | — | 215 ± 42 | 152 ± 23 |
| 40 | PG2 | ET7 | LR10% | 31 ± 2 | — | 241 ± 30 | 222 ± 32 |
| 41 | PG2 | ET7 | CB1% | 20 ± 1 | — | 125 ± 15 | 80 ± 8 |
| 42 | PG2 | ET7 | CB3% | 22 ± 3 | — | 209 ± 27 | 145 ± 17 |
| 43 | PG2 | ET7 | CB5% | 17 ± 1 | — | 173 ± 35 | 102 ± 11 |
| 44 | PG2 | ET7 | CB10% | 19 ± 2 | — | 141 ± 22 | 91 ± 13 |
| 45 | PG2 | ET7 | OA5% | — | — | 112 ± 22 | 138 ± 18 |
| 46 | PG2 | ET7 | M1% | — | — | 155 ± 49 | 116 ± 26 |
| 47 | PG2 | ET7 | M5% | — | — | 242 ± 47 | 143 ± 21 |
| 48 | PG2 | ET7 | M10% | — | — | 540 ± 87 | 425 ± 89 |
| 49 | PG2 | ET7 | M20% | — | — | 943 ± 36 | 911 ± 42 |
| 50 | ET98% | DB2% | — | — | — | 97 ± 7 | 93 ± 8 |
| 51 | DEG2 | ET7 | — | — | — | 14 ± 8 | 83 ± 5 |
| 52 | PEG2 | ET7 | — | — | — | 55 ± 9 | 58 ± 12 |
| 53 | PG2 | ET7 | P10% | 18 ± 2 | — | 436 ± 85 | 373 ± 71 |

Legend:
PG propylene glycol
PEG polyethylene glycol
ET ethyl alcohol
OC octanol
MT methanol
OA oleyl alcohol
M isopropyl myristate
LS lauryl sarkosine
LR laurylamide
CB cocamidopropyl betaine
DB dodecyl benzene sulfonate
DEG diethylene glycol
P isopropyl palmitate
Number of mice tested and number of test sites per mouse:
Tests 1–13: five mice, three sites each
Tests 14–22: four mice, three sites each
Tests 23–27: four mice, one site each
Test 28: three mice, one site each
Tests 29–32, 36–47 and 49–52: twelve mice, one site each
Tests 33–35: eleven mice, one site each
Tests 48 and 53: sixteen mice, one site each

We claim:

1. A method for topically administering a systemically and/or topically active agent through the skin or mucosal membrane of a terrestrial mammal, said method comprising administering said agent in a formulation containing a penetration enhancing amount of a composition comprising a glycol and an alcohol at a glycol:alcohol weight ratio ranging from about 1:0.1 to about 1:10, and a member selected from the group consisting of surfactants, branched-chain esters of fatty acids and membrane fluidizers.

2. A method in accordance with claim 1 in which said glycol is a member selected from the group consisting of ethylene glycol, propylene glycol, butylene glycol, glycerol, diethylene glycol, triethylene glycol, and polyethylene glycol.

3. A method in accordance with claim 1 in which said glycol is propylene glycol.

4. A method in accordance with claim 1 in which said alcohol is a $C_1$–$C_{18}$ saturated aliphatic alcohol.

5. A method in accordance with claim 1 in which said alcohol is a member selected from the group consisting of methanol, ethanol, propranol, isopropanol, and octanol.

6. A method in accordance with claim 1 in which said alcohol is a member selected from the group consisting of ethanol and octanol.

7. A method in accordance with claim 1 in which said alcohol is ethanol.

8. A method in accordance with claim 1 in which said alcohol is octanol.

9. A method in accordance with claim 1 in which said glycol:alcohol weight ratio is from about 1:1 to about 1:7.

10. A method in accordance with claim 1 in which said surfactant is a member selected from the group consisting of laurylamide, sodium dodecyl sulfate, dodecyl benzene sulfonate, lauryl sarkosine, and cocamidopropyl betaine.

11. A method in accordance with claim 1 in which said surfactant is laurylamide.

12. A method in accordance with claim 1 in which said surfactant is lauryl sarkosine.

13. A method in accordance with claim 1 in which said surfactant is sodium dodecyl sulfate.

14. A method in accordance with claim 1 in which said surfactant comprises from about 0.01% to about 25% of said formulation.

15. A method in accordance with claim 1 in which said surfactant comprises from about 0.2% to about 10% of said formulation.

16. A method in accordance with claim 1 in which said branched-chain ester of a fatty acid is an isopropyl ester of a $C_7$–$C_{24}$ carboxylic acid.

17. A method in accordance with claim 1 in which said branched-chain ester of a fatty acid is a member selected from the group consisting of isopropyl myristate and isopropyl palmitate.

18. A method in accordance with claim 1 in which said branched-chain ester of a fatty acid is isopropyl myristate.

19. A method in accordance with claim 1 in which said branched-chain ester of a fatty acid is isopropyl palmitate.

20. A method in accordance with claim 1 in which said branched-chain ester of a fatty acid comprises from about 0.1% to about 50% of said formulation.

21. A method in accordance with claim 1 in which said branched-chain ester of a fatty acid comprises from about 1.0% to about 20% of said formulation.

22. A method in accordance with claim 1 in which said membrane fluidizer is oleyl alcohol.

23. A method in accordance with claim 1 in which said formulation comprisesa membrane fluidizer at a concentration of from about 0.1% to about 25% of said formulation.

24. A method in accordance with claim 1 in which said formulation comprises a membrane fluidizer at a concentration of from about 1% to about 7% of said formulation.

25. A method for topically admininistering a systemically and/or topically active agent through the skin or mucosal membrane of a terrestrial mammal, said method comprising administering said agent in a composition which is a member selected from the group consisting of compositions a through r below:

| Major Components (abbreviation followed by parts by weight) | | Additional Components (abbreviation followed by weight percent relative to total composition) | | |
|---|---|---|---|---|
| Glycol | Alcohol | Branched-chain Ester | Surfactant | Membrane Fluidizer |
| a. PG1 | ET7 | M2 | — | OA5 |
| b. PG1 | ET7 | M2 | LS1.5 | — |
| c. PG1 | ET7 | M2 | LS3 | — |
| d. PG1 | ET7 | M2 | LS5 | — |
| e. PG1 | ET7 | M2 | LS5 | OA5 |
| f. PG1 | ET7 | M2 | LS10 | OA5 |
| g. PG1 | OC1 | — | SD3 | — |
| h. PG1 | ET2 | — | SD3 | — |
| i. PG1 | ET7 | — | SD3 | — |
| j. PG2 | ET7 | — | LR1 | — |
| k. PG2 | ET7 | — | LR3 | — |
| l. PG2 | ET7 | — | LR5 | — |
| m. PG2 | ET7 | — | LR10 | — |
| n. PG2 | ET7 | — | CB3 | — |
| o. PG2 | ET7 | P10 | — | — |
| p. PG2 | ET7 | M5 | — | — |
| q. PG2 | ET7 | M10 | — | — |
| r. PG2 | ET7 | M20 | — | — | in which the following abbreviations are used:
CB cocamidopropyl betaine
ET ethanol
LR laurylamide
LS lauryl sarkosine
M isopropyl myristate
OA oleyl alcohol
OC octanol
P isopropyl palmitate
PG propylene glycol
SD sodium dodecyl sulfate.

26. A method in accordance with claim 25 in which said composition is a member selected from the group consisting of:

| Major Components (abbreviation followed by parts by weight) | | Additional Components (abbreviation followed by weight percent relative to total composition) | | |
|---|---|---|---|---|
| Glycol | Alcohol | Branched-chain Ester | Surfactant | Membrane Fluidizer |
| PG1 | ET7 | M2 | LS5 | — |
| PG1 | ET7 | M2 | LS10 | OA5 |
| PG1 | ET2 | — | SD3 | — |
| PG2 | ET7 | — | LR1 | — |
| PG2 | ET7 | — | LR3 | — |
| PG2 | ET7 | P10 | — | — |
| PG2 | ET7 | M10 | — | — |

27. A method for topically administering a systemically and/or topically active agent through the skin or mucosal membrane of a terrestrial mammal, said method comprising administering said agent in a formulation containing a penetration enhancing amount of a composition comprising an alcohol having four or more carbon atoms and a member selected from the group consisting of glycols and surfactants.

28. A method in accordance with claim 27 in which said alcohol is selected from the group consisting of $C_4$–$C_{18}$ saturated aliphatic alcohols.

29. A method in accordance with claim 27 in which said alcohol is octanol.

30. A method in accordance with claim 27 in which said glycol is propylene glycol.

31. A method in accordance with claim 27 in which said alcohol and glycol are present in a weight ratio of from about 1:0.1 to about 1:10.

32. A method in accordance with claim 27 in which said alcohol and glycol are present in a weight ratio of from about 1:1 to about 1:7.

33. A method in accordance with claim 27 in which said surfactant is a member selected from the group consisting of laurylamide, sodium dodecyl sulfate, lauryl sarkosine, dodecyl benzene sulfonate, and cocamidopropyl betaine.

34. A method in accordance with claim 27 in which said surfactant is a member selected from the group consisting of laurylamide, lauryl sarkosine, and sodium dodecyl sulfate.

35. A method in accordance with claim 27 in which said composition comprises a surfactant at from about 0.2% to about 10% by weight of said composition.

36. A method in accordance with claim 27 in which said composition comprises a surfactant at about 3% by weight of said composition.

37. A method for topically administering a systemically and/or topically active agent through the skin or mucosal membrane of a terrestrial mammal, said method comprising administering said agent in a formulation containing a penetration enhancing amount of a composition comprising:

(a) propylene glycol:octanol in a weight ratio of 1:1, 1:3, or 1:7; and (b) octanol with 3% laurylamide, or octanol with 3% sodium dodecyl sulfate.

38. A method in accordance with claim 37 in which said composition is a member selected from the group consisting of octanol with 3% laurylamide, and octanol with 3% sodium dodecyl sulfate.

39. A transdermal and/or topical delivery composition for enhancing the penetration of a systemically and/or topically active agent through the skin or mucosal membrane of a terrestrial mammal, said composition comprising a glycol and an alcohol at a glycol:alcohol weight ratio ranging from about 1:0.1 to about 1:10 and a member selected from the group consisting of surfactants, branched-chain esters of fatty acids, and membrane fluidizers.

40. A composition in accordance with claim 39 in which said glycol is a member selected from the group consisting of ethylene glycol, propylene glycol, butylene glycol, glycerol, diethylene glycol, triethylene glycol, and polyethylene glycol.

41. A composition in accordance with claim 39 in which said glycol is propylene glycol.

42. A composition in accordance with claim 39 in which said alcohol is a $C_1$–$C_{18}$ saturated aliphatic alcohol.

43. A composition in accordance with claim 39 in which said alcohol is a member selected from the group consisting of methanol, ethanol, propranol, isopropanol, and octanol.

44. A composition in accordance with claim 39 in which said alcohol is a member selected from the group consisting of ethanol and octanol.

45. A composition in accordance with claim 39 in which said alcohol is ethanol.

46. A composition in accordance with claim 39 in which said alcohol is octanol.

47. A composition in accordance with claim 39 in which said glycol:alcohol weight ratio is from about 1:1 to about 1:7.

48. A composition in accordance with claim 39 in which said surfactant is a member selected from the group consisting of laurylamide, sodium dodecyl sulfate, dodecyl benzene sulfonate, lauryl sarkosine, and cocamidopropyl betaine.

49. A composition in accordance with claim 39 in which said surfactant is laurylamide.

50. A composition in accordance with claim 39 in which said surfactant is lauryl sarkosine.

51. A composition in accordance with claim 39 in which said surfactant is sodium dodecyl sulfate.

52. A composition in accordance with claim 39 in which said surfactant comprises from about 0.01% to about 25% of said formulation.

53. A composition in accordance with claim 39 in which said surfactant comprises from about 0.2% to about 10% of said formulation.

54. A composition in accordance with claim 39 in which said branched-chain ester of a fatty acid is an isopropyl ester of a $C_7$–$C_{24}$ carboxylic acid.

55. A composition in accordance with claim 39 in which said branched-chain ester of a fatty acid is a member selected from the group consisting of isopropyl myristate and isopropyl palmitate.

56. A composition in accordance with claim 39 in which said branched-chain ester of a fatty acid is isopropyl myristate.

57. A composition in accordance with claim 39 in which said branched-chain ester of a fatty acid is isopropyl palmitate.

58. A composition in accordance with claim 39 in which said branched-chain ester of a fatty acid comprises from about 0.1% to about 50% of said formulation.

59. A composition in accordance with claim 39 in which said branched-chain ester of a fatty acid comprises from about 1.0% to about 20% of said formulation.

60. A composition in accordance with claim 39 in which said membrane fluidizer is oleyl alcohol.

61. A composition in accordance with claim 39 in which said formulation comprises a membrane fluidizer at a concentration of from about 0.1% to about 25% of said formulation.

62. A composition in accordance with claim 1 in which said formulation comprises a membrane fluidizer at a concentration of from about 1% to about 7% of said formulation.

63. A composition for enhancing the penetration of a systemically and/or topically active agent through the skin or mucosal membrane of a terrestrial mammal, said composition comprising administering said agent in a composition which is a member selected from the group consisting of compositions a through r below:

| | Major Components (abbreviation followed by parts by weight) | | Additional Components (abbreviation followed by weight percent relative to total composition) | | |
|---|---|---|---|---|---|
| | Glycol | Alcohol | Branched-chain Ester | Surfactant | Membrane Fluidizer |
| a. | PG1 | ET7 | M2 | — | OA5 |
| b. | PG1 | ET7 | M2 | LS1.5 | — |
| c. | PG1 | ET7 | M2 | LS3 | — |
| d. | PG1 | ET7 | M2 | LS5 | — |
| e. | PG1 | ET7 | M2 | LS5 | OA5 |
| f. | PG1 | ET7 | M2 | LS10 | OA5 |
| g. | PG1 | OC1 | — | SD3 | — |
| h. | PG1 | ET2 | — | SD3 | — |
| i. | PG1 | ET7 | — | SD3 | — |
| j. | PG2 | ET7 | — | LR1 | — |
| k. | PG2 | ET7 | — | LR3 | — |
| l. | PG2 | ET7 | — | LR5 | — |
| m. | PG2 | ET7 | — | LR10 | — |
| n. | PG2 | ET7 | — | CB3 | — |
| o. | PG2 | ET7 | P10 | — | — |
| p. | PG2 | ET7 | M5 | — | — |
| q. | PG2 | ET7 | M10 | — | — |
| r. | PG2 | ET7 | M20 | — | — | in which the following abbreviations are used:

CB cocamidopropyl betaine

ET ethanol

LR laurylamide

LS lauryl sarkosine

M isopropyl myristate

OA oleyl alcohol

OC octanol

P isopropyl palmitate

PG propylene glycol

SD sodium dodecyl sulfate.

64. A composition in accordance with claim 63 in which said composition is a member selected from the group consisting of:

| Major Components (abbreviation followed by parts by weight) | | Additional Components (abbreviation followed by weight percent relative to total composition) | | |
|---|---|---|---|---|
| Glycol | Alcohol | Branched-chain Ester | Surfactant | Membrane Fluidizer |
| PG1 | ET7 | M2 | LS5 | — |
| PG1 | ET7 | M2 | LS10 | OA5 |
| PG1 | ET2 | — | SD3 | — |
| PG2 | ET7 | — | LR1 | — |
| PG2 | ET7 | — | LR3 | — |
| PG2 | ET7 | P10 | — | — |
| PG2 | ET7 | M10 | — | — |

65. A composition for enhancing the penetration of a systemically and/or topically active agent through the skin or mucosal membrane of a terrestrial mammal, said composition comprising administering said agent in a formulation containing a penetration enhancing amount of a composition comprising an alcohol having four or more carbon atoms and a member selected from the group consisting of glycols and surfactants.

66. A composition in accordance with claim 65 in which said alcohol is selected from the group consisting of $C_4$–$C_{18}$ saturated aliphatic alcohols.

67. A composition in accordance with claim 65 in which said alcohol is octanol.

68. A composition in accordance with claim 65 in which said glycol is propylene glycol.

69. A composition in accordance with claim 65 in which said alcohol and glycol are present in a weight ratio of from about 1:0.1 to about 1:10.

70. A composition in accordance with claim 65 in which said alcohol and glycol are present in a weight ratio of from about 1:1 to about 1:7.

71. A composition in accordance with claim 27 in which said surfactant is a member selected from the group consisting of laurylamide, sodium dodecyl sulfate, lauryl sarkosine, dodecyl benzene sulfonate, and cocamidopropyl betaine.

72. A composition in accordance with claim 65 in which said surfactant is a member selected from the group consisting of laurylamide, lauryl sarkosine, and sodium dodecyl sulfate.

73. A composition in accordance with claim 65 in which said composition comprises a surfactant at from about 0.2% to about 10% by weight of said composition.

74. A composition in accordance with claim 65 in which said composition comprises a surfactant at about 3% by weight of said composition.

75. A composition for enhancing the penetration of a systemically and/or topically active agent through the skin or mucosal membrane of a terrestrial mammal, said composition comprising administering said agent in a formulation containing a penetration enhancing amount of a composition comprising:

(a) propylene glycol:octanol in a weight ratio of 1:1, 1:3, or 1:7; and (b) octanol with 3% laurylamide, or octanol with 3% sodium dodecyl sulfate.

76. A composition in accordance with claim 75 in which said composition is a member selected from the group consisting of octanol with 3% laurylamide, and octanol with 3% sodium dodecyl sulfate.

* * * * *

UNITED STATES PATENT AND TRADEMARK OFFICE
CERTIFICATE OF CORRECTION

PATENT NO. : 5,760,096
DATED : June 2, 1998
INVENTOR(S) : Carl R. Thornfeldt et al It is certified that error appears in the above-identified patent and that said Letters Patent is hereby corrected as shown below:

On the title page, item [56], insert the following:

U. S. PATENT DOCUMENTS

| EXAMINER INITIAL | PATENT NUMBER | ISSUE DATE | PATENTEE | CLASS | SUBCLASS | FILING DATE IF APPROPRIATE |
|---|---|---|---|---|---|---|
| | 4 2 6 3 2 7 4 | 21 Apr 1981 | A. B. Kalkarni et al. | | | |
| | 3 9 8 2 0 2 2 | 21 Sep 1976 | G. Hool et al. | | | |

FOREIGN PATENT OR PUBLISHED FOREIGN PATENT APPLICATION

| | | DOCUMENT NUMBER | PUBLICATION DATE | COUNTRY OR PATENT OFFICE | CLASS | SUBCLASS | TRANSLATION YES | NO |
|---|---|---|---|---|---|---|---|---|
| | | WO 95 /0 5 1 5 9 | 23 Feb 1995 | PCT | | | | |
| | | 0 3 6 8 4 0 9 | 16 May 1990 | EPO | | | | |
| | | 6 -2 5 6 2 1 8 | 13 Sep 1994 | Japan | | | | |
| | | 4 -2 3 4 3 1 4 | 24 Aug 1992 | Japan | | | | |

Signed and Sealed this

Sixteenth Day of February, 1999

Attest:

Attesting Officer

*Acting Commissioner of Patents and Trademarks*